United States Patent [19]

Soto-Tolosa et al.

[11] Patent Number: 5,514,114

[45] Date of Patent: May 7, 1996

[54] INTRAVASCULAR PUNCTURING NOZZLE WITH AN AUTOMATIC NO BLOOD REFLUX MECHANISM

[76] Inventors: Marcos Soto-Tolosa; Pere Arques-Teixidor, both of Coón 20, 08184-Palau De Plegamans (Barcelona), Spain

[21] Appl. No.: 290,309

[22] Filed: Aug. 12, 1994

[30] Foreign Application Priority Data

Aug. 17, 1993 [ES] Spain ..................................... P9301813

[51] Int. Cl.⁶ ..................................... A61M 5/18
[52] U.S. Cl. ........................ 604/275; 606/185; 604/249; 604/250
[58] Field of Search ..................................... 604/167, 169, 604/245, 246, 249, 248, 171, 164, 264, 250, 275; 606/185, 167, 184

[56] References Cited

U.S. PATENT DOCUMENTS 5,098,394  3/1992  Luther ..................................... 604/167
5,209,737  5/1993  Ritchart et al. ........................ 604/167
5,290,245  3/1994  Dennis ..................................... 604/167

*Primary Examiner*—Stephen C. Pellegrino
*Assistant Examiner*—Glenn Dawson

[57] ABSTRACT

An intravascular puncturing nozzle with an automatic no blood reflux mechanism. The mechanism includes a part (3) resiliently biased towards a position closing the passage (6) of the plastic nozzle (2), which position is automatically reached when the needle (4) puncturing the blood vessel is removed from such passage. The connector (5) on the serum equipment automatically opens the passage (6) when the said equipment is connected. The mechanism is applicable to intravascular puncturing nozzles to prevent the patient's blood from refluxing and coming into contact with the operator, thereby avoiding contagion, and in order not to put the sterility of the material used at stake.

2 Claims, 2 Drawing Sheets

INTRAVASCULAR PUNCTURING NOZZLE WITH AN AUTOMATIC NO BLOOD REFLUX MECHANISM

FIELD OF THE INVENTION

The present invention relates to an intravascular puncturing nozzle with an automatic no blood reflux mechanism which, in addition to the function for which it is designed, affords a number of advantages discussed hereinafter, and others that are inherent in its organization and construction.

BACKGROUND OF THE INVENTION

Existing intravascular nozzles or catheters, being the prior art, comprise a plastic material tube with an end designed to be housed within the punctured blood vessel and its other end connecting with a serum equipment via a "Luer-lock" system. Running along the inside of the nozzle is the needle allowing puncture and fitted at its far end with a receptacle which on being filled indicates that the needle is correctly positioned within the blood vessel.

Once the blood vessel has been punctured the needle is removed and the plastic nozzle is inserted until it reaches its definitive position. The serum equipment is finally connected at the end of the nozzle via the so-called "Luer-lock" system.

This latter operation, even if carried out skillfully and at great speed, usually entails the outlet of drops or indeed greater quantities of blood. This means that the operator will come into contact with the patient's blood and hence there will clearly be a risk of contamination and contagion if the patient carries any infectious diseases (hepatitis, AIDS, and so forth). In any event, even if there are no chances of contagion, the need to clean the area stained by the refluxing blood will always be a problem and the sterility of the material used will moreover be at stake.

SUMMARY OF THE INVENTION

The applicants for this Patent of Invention have devised an intravascular puncturing nozzle fitted with an automatic mechanism designed to prevent blood reflux, in order to correct the disadvantages and problems set out above, stemming from the use of currently known conventional nozzles.

The mechanism is constructed to allow its being housed within the cone of the plastic nozzle, viz. at the end connecting with the serum equipment.

Broadly speaking, the mechanism comprises a part that is drawn by resilient means towards a closed position blocking the passage in the plastic nozzle. In accordance with the above, when the needle is removed the said part closes the said passage and prevents the blood from refluxing. The opposition of the said resilient means is automatically overcome when the serum equipment is connected, allowing administration to the patient.

The nozzle subject of the present Patent of Invention affords the aforesaid advantages, and others that will be easily inferred from the embodiment described hereinafter in further detail to expedite the understanding of the features set out above, contemporaneously giving a number of details, this specification carrying attached to this end a number of drawings illustrating a practical embodiment of the invention, as an example only, without limiting the scope of such invention. Further scope of applicability of the present invention will become apparent from the detailed description given hereinafter. However, it should be understood that the detailed description and specific examples, while indicting preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus are not limitative of the present invention, and wherein:

DESCRIPTION OF AN EMBODIMENT ACCORDING TO THE INVENTION

Figure 1:
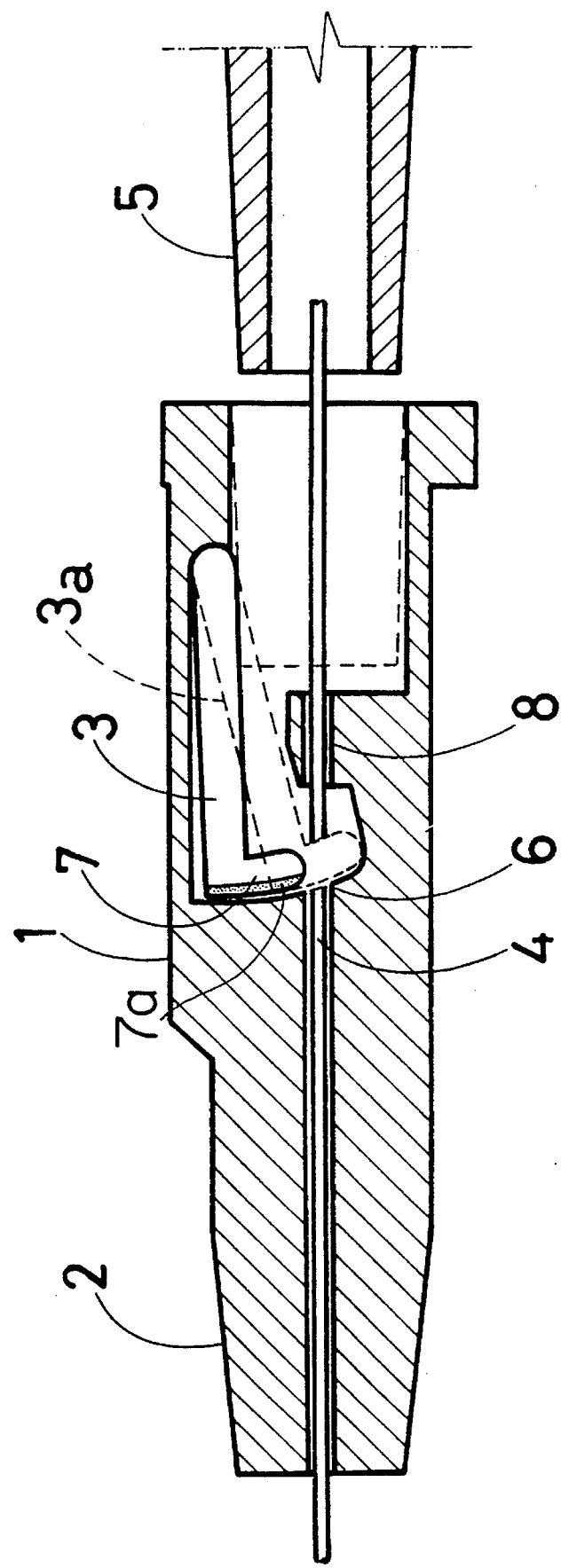
FIG. 1 is a longitudinal section showing a puncturing nozzle fitted with the automatic no blood reflux mechanism in accordance with a first embodiment.

As shown in FIG. 1 the intravascular puncturing nozzle comprises a mechanism housed inside the cone -1- of the plastic nozzle -2- at the end connecting with the serum equipment. The mechanism as such is comprised by a part -3-, L-shaped in the embodiment, automatically closing the passage -6- of the plastic nozzle, when the needle -4- is removed, preventing the blood from refluxing and opening automatically when the serum equipment is connected, allowing administration thereof to the patient.

The part -3- works as a lever-gate which is held connected to resilient biasing means that are not shown, which could comprise a spring, rubber parts and the like. The part -3-, when at rest, has its heel or shorter side -7- lying on the needle -4- that is used to puncture the vessel, and hence when the needle is removed the part -3- rapidly reaches position -3a- at which the said heel -7- blocks the passage of blood to the outside. This situation can be sustained for a long time and there is hence no need to work at an undue speed during the operation. At this position the part -3- projects slightly from the cone -1- of the plastic nozzle, which allows the part -3- to be driven, when the serum equipment is connected, by the connector -5- existing at the end of such equipment, opening the way for the serum to be administered normally.

Figure 2:
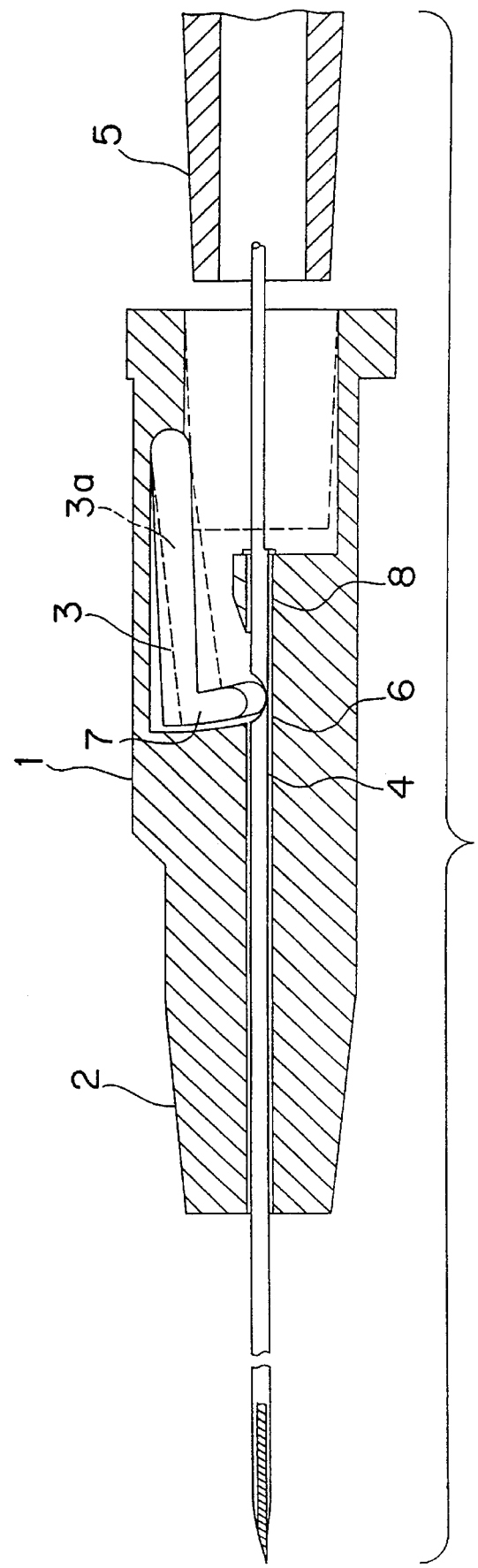
FIG. 2 is a longitudinal section showing a puncturing nozzle fitted with the automatic no blood reflux mechanism in accordance with a second embodiment.

In the second embodiment shown in FIG. 2, the part -3- can press against a fine plastic tube placed at the gate area -6- in such a way that the blood when flowing inside the tube will not come into contact with the part -3-. In this case, it would be necessary to increase the power of the resilient biasing means of the part -3-.

It is also possible to provide two simultaneous drive parts, each covering one-half of the flow, or each covering all of the flow, at adjacent positions, as a double valve.

The portion -7- of the part -3- which blocks the flow of blood, can be coated with an absorbing material 7a enhancing its effectiveness or otherwise. Furthermore, this absorbing material can be applied to other points attached to the mechanism, such as the end part -8- of the puncturing needle run.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An intravascular nozzle assembly for use with a puncturing needle and serum equipment, said nozzle assembly comprising:

a plastic nozzle having a first end portion insertable within a punctured blood vessel, a second opposed end connectable with a connector of said serum equipment, and a cone portion located between said first end and said second end; and a blood reflux prevention device located within said cone portion, said blood reflux prevention device movable between an open position allowing blood flow therepast and a closed position for preventing blood flow therepast, a portion of said blood reflux prevention device having an absorbing material coating for further preventing blood flow therepast when in said closed position, said blood reflux prevention device being automatically moved to said closed position when said puncturing needle is removed from said nozzle, and being automatically moved to said open position upon insertion of said connector into said second end.

2. An intravascular nozzle assembly for use with a puncturing needle and serum equipment, said nozzle assembly comprising:

a plastic nozzle having a first end portion insertable within a punctured blood vessel, a second opposed end connectable with a connector of said serum equipment, and a cone portion located between said first end and said second end;

a plastic tube located coaxially within said cone portion; and a blood reflux prevention device located within said cone portion, said blood reflux prevention device movable between an open position allowing blood flow therepast and a closed position wherein said blood reflux prevention device presses against said plastic tube for preventing blood flow therepast, said blood reflux prevention device being automatically moved to said closed position when said puncturing needle is removed from said nozzle, and being automatically moved to said open position upon insertion of said connector into said second end.

* * * * *